United States Patent [19]
Stiffey et al.

[11] Patent Number: 5,580,785
[45] Date of Patent: Dec. 3, 1996

[54] FIELD-PORTABLE TOXICITY TESTER

[75] Inventors: Arthur V. Stiffey; Thomas G. Nicolaids, both of Slidell, La.

[73] Assignee: Lumitox Gulf L.C., New Orleans, La.

[21] Appl. No.: 430,749

[22] Filed: Apr. 27, 1995

[51] Int. Cl.⁶ .......................... C12M 1/34; C12M 1/36; C12M 1/02

[52] U.S. Cl. .................. 435/288.7; 435/286.7; 435/8; 422/52

[58] Field of Search .............. 435/8, 9, 30, 287.1, 435/286.7, 288.1, 288.7; 422/52, 68; 250/361 R, 361 C, 461.2, 461.1; 356/244, 417; 436/172

[56] References Cited

U.S. PATENT DOCUMENTS

| | | | |
|---|---|---|---|
| 3,359,973 | 12/1967 | Hoffman | 435/288.7 |
| 3,370,175 | 2/1968 | Jordon et al. | 435/288.7 |
| 3,726,599 | 4/1973 | Neary | 422/52 |
| 3,797,999 | 3/1974 | Witz et al. | 435/288.7 |
| 4,099,920 | 7/1978 | Heiss | 422/52 |
| 4,142,859 | 3/1979 | Shaffer | 435/288.7 |
| 4,372,683 | 2/1983 | Sternberg | 435/288.7 |
| 4,396,579 | 8/1983 | Schroeder et al. | 435/288.7 |
| 4,563,331 | 1/1986 | Losee et al. | 435/288.7 |
| 4,672,039 | 6/1987 | Lundblom | 422/52 |
| 4,689,305 | 8/1987 | Stiffey et al. | 435/291 |
| 4,950,594 | 8/1990 | Stiffey | 435/32 |
| 5,223,218 | 6/1993 | Fukuokea et al. | 422/52 |
| 5,264,906 | 11/1993 | Ferer et al. | 422/52 |

OTHER PUBLICATIONS

Qwiklite Assays, published by Naval Comand Control and Ocean Surveillance Center, San Diego, CA 92152–5001 Sep. 1993.

Qwiklite Bioassay System, published by Naval Comand Control and Ocean Survellance Center, San Diego, CA 92152–5001 Sep. 1994.

Primary Examiner—William Beisner
Attorney, Agent, or Firm—Thomas M. Phillips

[57] ABSTRACT

A portable toxicity tester for use in the field using bioluminescent organisms consisting of a light tight container for housing the necessary flash of light detecting apparatus and the necessary signal processing circuits, digital readout and control panel. A light tight chamber is provided with a removable stirrer assembly which is the stirrer motor housing as well as the light tight cover for the chamber. With the cover removed, a vial containing the necessary inoculated bioluminescence organisms is inserted into a holder in the chamber. Part of the stirrer assembly is a paddle attached to the motor shaft that extends to near the bottom of the vial. The top of the vial holder extends beyond the outer surface of the cover to insure a light tight seal.

7 Claims, 3 Drawing Sheets

FIELD-PORTABLE TOXICITY TESTER

BACKGROUND OF THE INVENTION

1. Field of the Invention

The present invention relates to the testing for the presence of toxic substances and more particularly to a new, inexpensive, portable, hand held means for testing in a field environment for the presence of toxic substances involving the use of the microscopic, bioluminescent marine organisms.

2. Description of the Prior Art

Bioluminescence has been the subject of considerable research, and its measurement for the most part has been by a relatively complex photomultiplier photometer designed by McNicholls in 1952, Methods Biochem Anal. 861; modified subsequently by Mitchell, Hastings and Strickland, "A practical Handbook of Seawater Analysis," 2nd ed. Bull. 167, Fisheries Research Board of Canada; and most recently by Stiffey et al. There are many commercially available photometers, but all are expensive; are not adaptable for field operations; and can detect only intermittent light emissions.

For example, the tester described in U.S. Pat. No. 4,950,594 issued to Stiffey et al, Aug. 21, 1990 requires the samples of suspected toxic substances to be transported over long distances to a laboratory environment, for example, oil well drilling fluids used in offshore oil well drilling operations. Also this procedure had to be carried out in a darkened room to prevent extraneous light from reaching the photomultiplier tube and to reduce desensitization of the organisms by exposure to light. Many toxins tend to degrade while being transported from the field to the laboratory, thus leading to detoxification and consequently misleading test results.

SUMMARY OF THE INVENTION

The present invention provides for a new, inexpensive, portable, hand held device that can be taken to the field to test substances for toxicity, thus, overcoming the disadvantages of the prior known means of performing the test for toxicity. The present invention employs a solution containing a measured number of bioluminescent dinoflagellate. The solution is transported in vials to the field location of the suspected toxic substance. A sample of the substance to be tested for toxicity is then added to the solution in the vial.

The novel testing photometer is contained in a light tight container having a port for receiving the vial containing the mixture of the solution and the substance to be tested. The vial is held in a vial holder. The vial holder is positioned with respect to the receiving port opening so that when the cover containing a motor stirrer assembly including a paddle is positioned to cover the port, the vial is light tight and the paddle extend into the vial sufficiently so that when the paddle rotates, a shearing action will occur. A light sensing apparatus and circuitry detects and processes any detected flash of light received from the vial in response to the shearing action. Means are provided for measuring the magnitude of the flash of light in a sensed pulse mode or in a signal integrated mode.

Accordingly, an object of the invention is the provision of an inexpensive hand held portable photometer for the detection and quantification of low level light emissions from bioluminescent organisms for the testing of the presence of toxic substances.

Other objects, advantages and novel features of the invention will become apparent from the following detailed description of the invention when considered in conjunction with the accompanying drawing wherein:

DESCRIPTION OF THE PREFERRED EMBODIMENT

Figure 2:
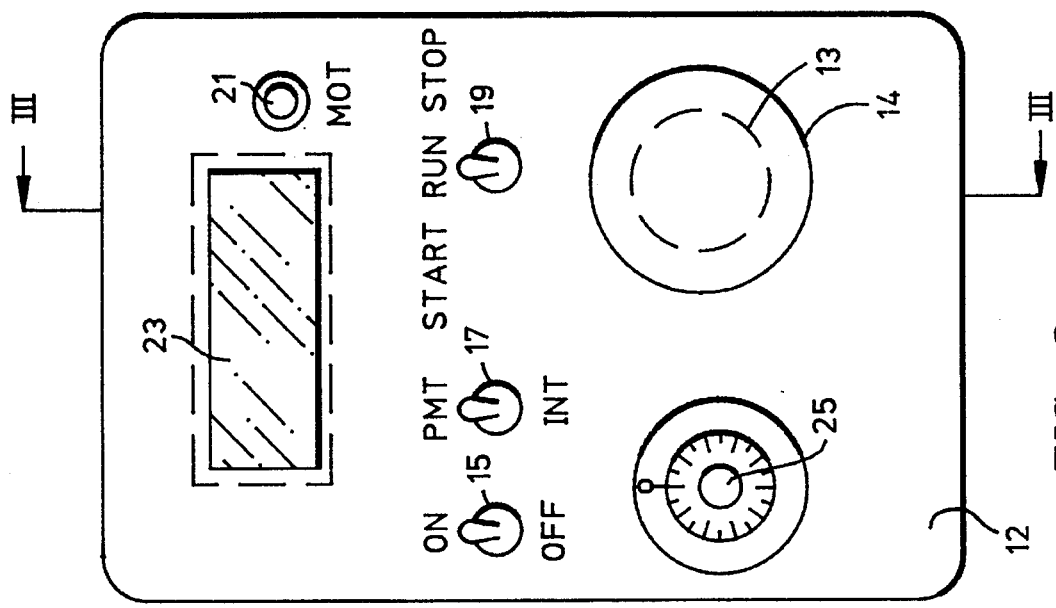
FIG. 2 is a plan view of the embodiment of FIG. 1 particularly showing the control panel and the digital readout.
Figure 1:
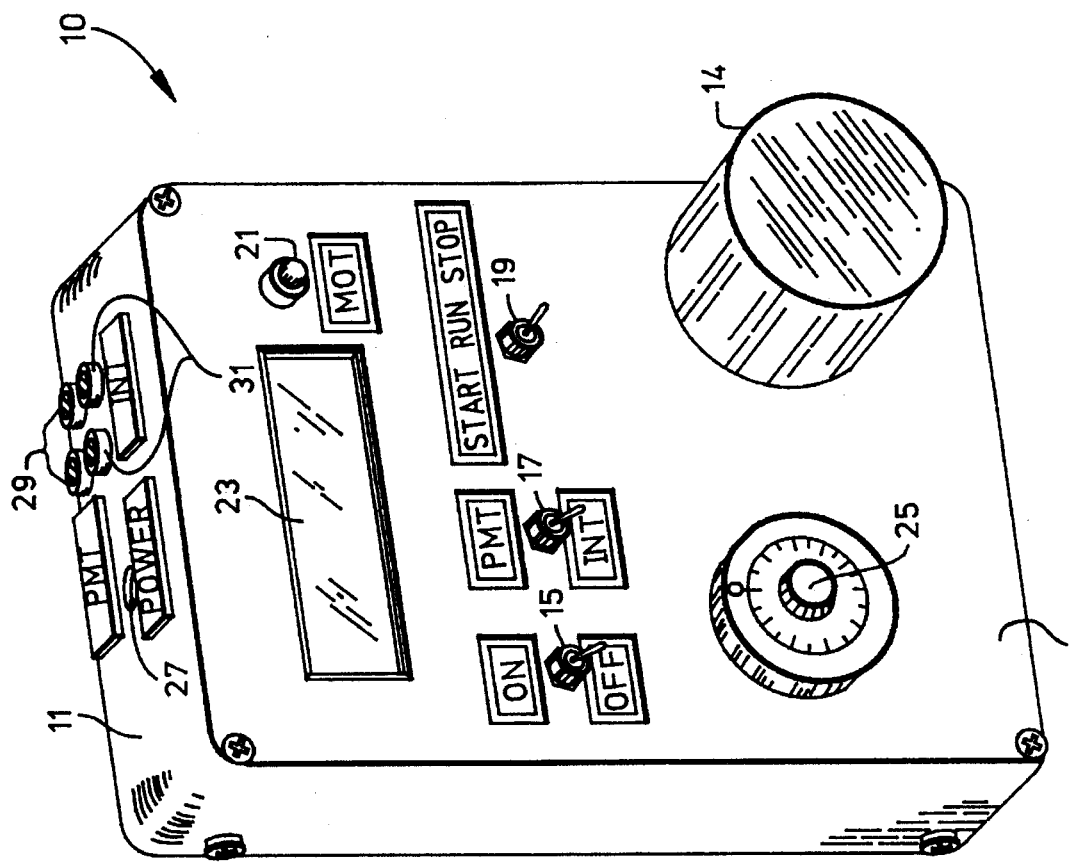
FIG. 1 is a perspective view of the photometer in accordance with the teachings of the invention.

Referring now to FIGS. 1 and 2, wherein there is shown a covered enclosure 10 consisting of a box shaped container 11 and a cover 12. Attached to cover 12 are a motor housing and port cover 14, motor 13, power on-off switch 15, PMT-INT selector switch 17, START-RUN-STOP switch 19, motor running indicator light 21, digital display window 23, and turn selector knob 25. Power input connector 27, and output connectors 29 and 31 for PMT and INT are also provided.

Figure 3:
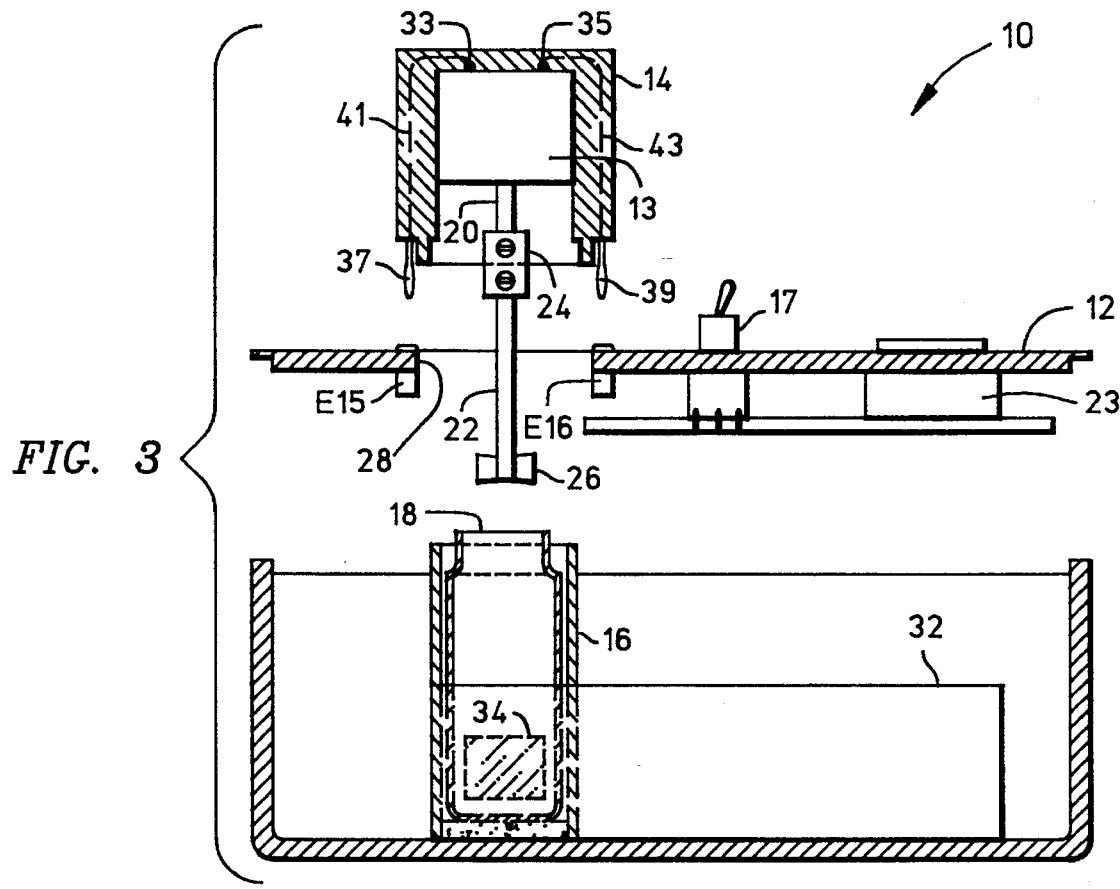
FIG. 3 is a sectional view along the line III—III of FIG. 2.

Referring now to FIG. 3, which shows in more detail the assembly of the invention. Referring now to the interior of container 11, therein is shown a vial holder 16 into which vial 18 is inserted. Vial 18 can be inserted or removed through a port or opening 21 in cover 12. Vial holder 16, in practice, is an approximate 1.25 inch, inside diameter tube made of clear plastic of about 1/16 inch wall thickness and extends about ½ inch above cover 12. The portion extending above cover 12 is painted black. Motor housing and cover 14 is recessed internally to fit snugly over protruding tube 16 effectively excluding light. Motor 13, vial holder 16 and port 28 are substantially of the same diameter. Power is supplied to motor 13 terminals 33 and 35 by means of connectors E15 and E16 (also shown in FIG. 4.), connectors 37 and 39, and conductors 41 and 43. An extension shaft 22 is coupled to motor shaft 20 by means of a coupler 24 and has a paddle 26 attached to the free end. When cover 14 is in place, covering port access port 28 paddle 26 will extend sufficiently into vial 18 for agitating the solution when the motor 13 is rotating.

Paddle 26 and shaft 22 are coated with plastic to eliminate any reaction between the test organisms and the metal.

Figure 4A:
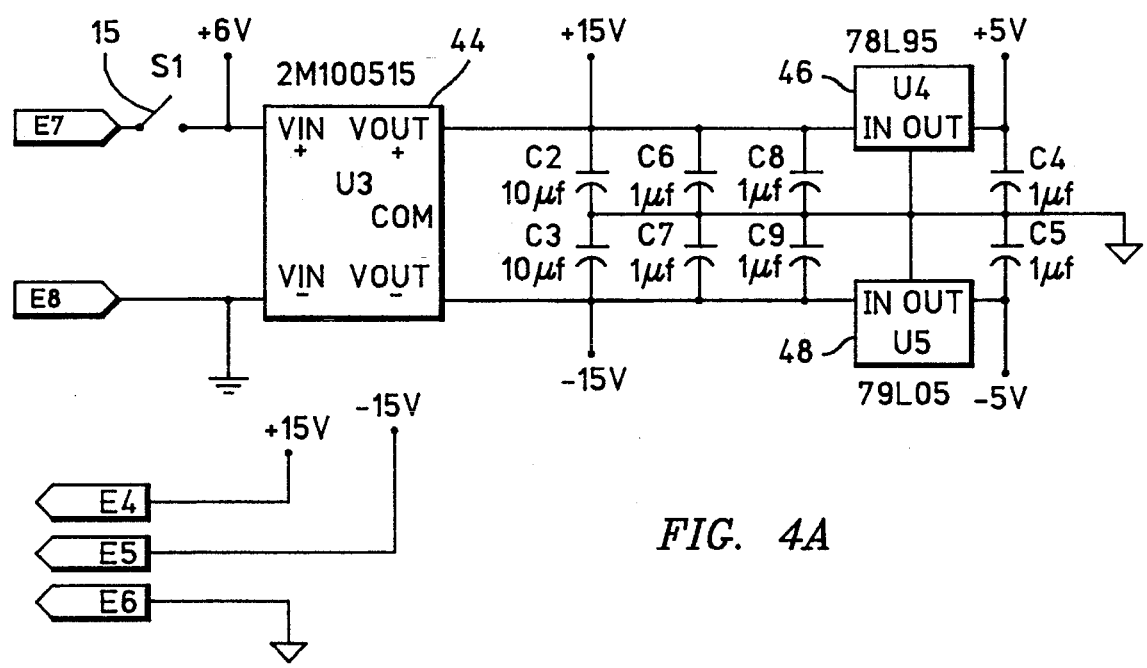
FIGS. 4A and 4B are schematic diagrams of the circuit contained on the circuit board shown in FIG. 2.

As shown in FIG. 4A, power is supplied through switch 15 from any suitable 6 volt power source such as a battery pack, a 12-volt DC step-down transformer operated from a vehicles's cigarette-lighter socket, or by a 110-volt AC to 6-volt step-down transformer. The 6 volt power source is plugged into connector 27 (shown in FIG. 1). A DC to DC converter 44 supplies +/–15 volts DC to voltage regulators 46 and 48 to provide +/–5 volts DC to the light emission diode (LED) panel meter 50(FIG. 4B).

Figure 4B:
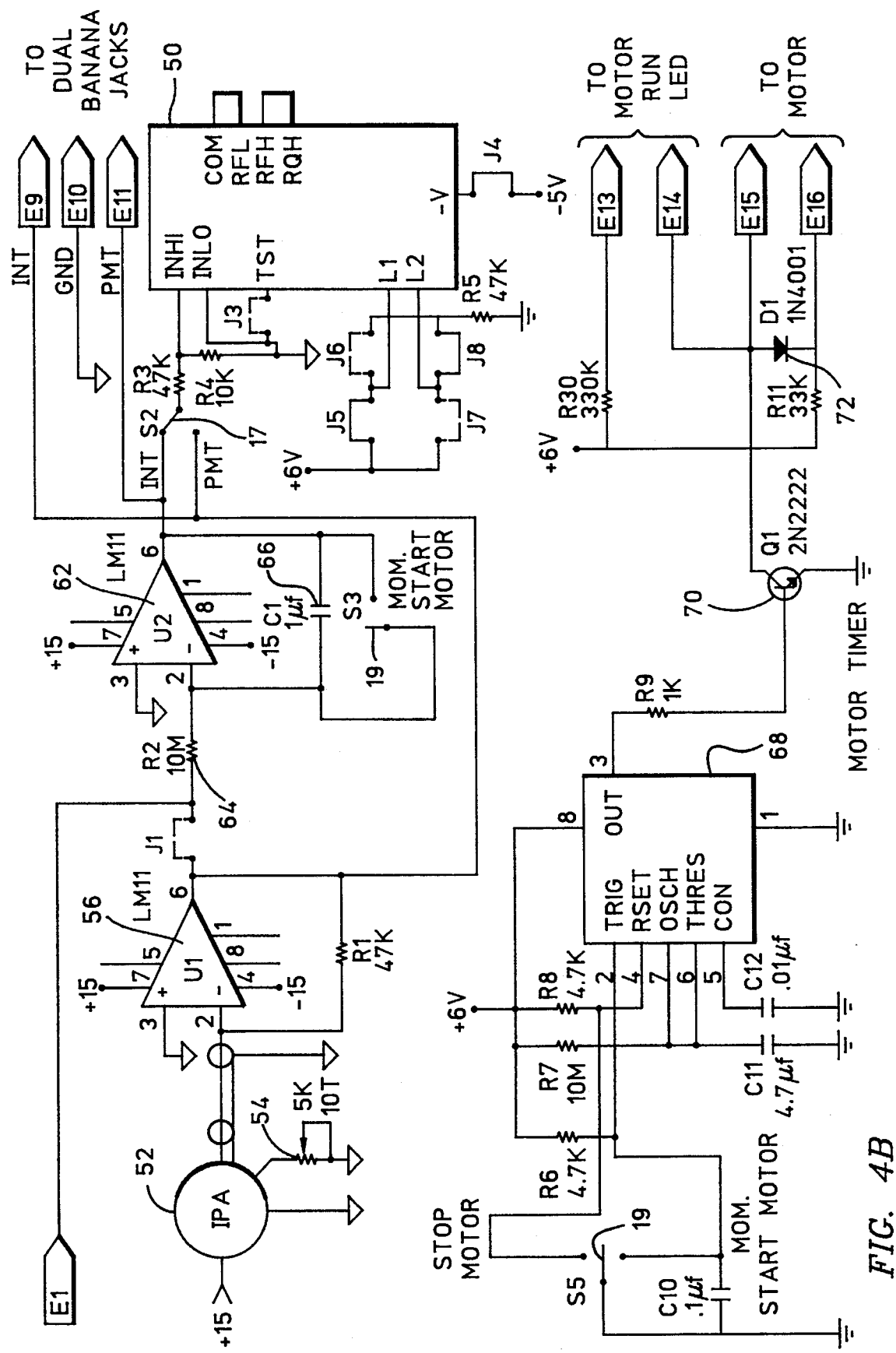

Referring to FIG. 4B, high voltage for photomultiplier tube 32 (FIG. 3) is generated internally by the integrated photomultiplier assembly (IPA) 52 which is by way of example a Hammamatsu part number H957-06. Assembly 52 contains the photomultiplier tube 32, a voltage divider, a DC—DC converter and a magnetic shield (not shown).

Power supplied to assembly 52 is +15 volt DC supplied from converter 44. Plate voltage up to 1100 volts is generated internally and is controlled by the 5K, 10 turn potentiometer 54 by means of control counter dial 25 (FIG. 1). Since plate voltage determines the sensitivity of photomultiplier tube 32, potentiometer 54 is the sensitivity control of the novel photometer.

The output from assembly 52 is the cathode and flows to the summing junction of operational amplifier 56 which is connected as an inverting amplifier. The output voltage of operational amplifier 56 is proportional to the light level detected by integrated photomultiplier assembly 52. This voltage may be monitored externally through connector terminal 29(FIG. 1), or by light emission panel meter 50 when switch 17 is in the PMT position.

Output of operational amplifier 56 is processed by an integrator circuit composed of operational amplifier 62, 10-M$\Omega$ resistor 64 and 1-$\mu$f capacitor 66. The integrator sums the total integrator circuit composed of operational amplifier 62,10-M$\Omega$ resistor 64 and 1-$\mu$f capacitor 66. The integrator sums the total amount of light produced by the sample over time.

It has been determined empirically that one minute is sufficient to exhaust the bioluminescent light source; therefore, operation is limited by the 60-second timer circuit 68. The output of timing circuit 68 turns on transistor 70 for 60 seconds to drive motor 13(FIG. 3). Diode 72 is a protector connected across leads E15 and E16 to prevent fly back voltage when motor 13 is turned off.

Switch 19 is a spring loaded double pole double throw switch and when it is moved to the momentary start motor-(MOM. START MOTOR) position, capacitor 66 is shorted to reset timming circuit 68 to zero. Voltage output from operational amplifier 62 is proportional to the total amount of light detected by IPA 52. This voltage may be monitored externally through connector terminal 31 or by LED meter 50 when switch 17 is in the integrated position. The LED meter 50 is powered by +/−5 volts DC and measures +/−2 volts DC. In practice, it is a 3½ -digit meter. As such, it measures 0 to +/−1999 (2000 counts for each polarity). "Over" range is indicated by a "1" in the most significant digit when none of the other digits is illuminated.

SUMMARY

In practice, the tester is accompanied to the field by a small cooler carrying test vials containing test media with pre-counted organisms. They can survive for at least a week at room temperature in a field location. Some are sample-inoculated with a 50 $\mu$l mechanical pipette and incubated for about an hour before testing begins. Housing 14 is removed and a vial containing an inoculated sample is inserted into vial holder 16. Housing 14 is then replaced to provide a light tight chamber. Stirrer paddle 26 nearly reaches the bottom of vial 18. The test is started by moving switch 15 to the ON position. Next, spring loaded switch 19 is moved momentarily to START position and released. This starts timing circuit 68(FIG. 4B) which supplies power to stirrer motor 13 for 1 minute. Because it is spring loaded, switch 19 relaxes to the RUN position. Power is also supplied to indicator light 21 indicating that motor 13 has power. Stirrer motor 13 turns at about 500 rpm for one minute, which is enough time to exhaust all of the cell's bioluminescence. Emitted light is detected by PMT 32, which transmits a signal to the electronic circuit that integrates, cumulatively. The resultant value is displayed digitally on meter 50 or as a curve on a strip chart (not shown)but would be connected to output terminal 31(see FIG. 1).

In practice and by way of example, the following components have been found to be satisfactory:

| | |
|---|---|
| IPA Assembly 52 | Hammamatsu part No. H957-06 |
| Digital volt meter 50 | Modutec part No. BL-30030201 |
| Potentiometer 54 | Bourns part No. 35905-5K |
| Turns counter 25 | Bourns part No. H-507-6 |

Obviously many modifications and variations of the present invention are possible in light of the above teachings. It is therefore to be understood that within the scope of the appended claims the invention may be practiced otherwise than as specifically described.

What is claimed is:

1. A portable self-contained hand held tester for testing, in a field environment, the presence of a toxic contaminant by the use of bioluminescent organisms including:

a light tight container having a removable cover;

said container having incorporated therein a vial holder of a predetermined circumference for supporting a vial containing a sample, which may contain a contaminant;

said removable cover having a port with a circumference slightly larger than the circumference of said vial holder and being so disposed that said vial holder extends beyond the top edge of said cover by a predetermined distance and permitting inserting and removing said vial in and out of said vial holder respectively;

removable motor housing means for covering said port to prevent light from entering said vial;

said motor housing means having electrical contacts, an electric motor and electric motor driven means for agitating the contents of said vial, said container cover having electrical contacts so disposed to mate with said motor housing electrical contacts when said motor housing means is positioned to close said port and is in position to provide a light tight cover of said port whereby electrical power is provided to said motor;

said container further containing therein light sensing apparatus and electrical circuitry for detecting and processing any flash of light emitted from said vial in response to the shearing action caused by said agitation.

2. The tester of claim 1 wherein said electrical circuit contains a timer for limiting the period of time which the sample is agitated by the electric motor.

3. The tester of claim 2 wherein is provided a start switch which is manually operated to initiate said timer.

4. The tester of claim 3 wherein said start switch has a start position, a run position and a stop position, whereby said start switch relaxes to the run position when said stop switch is manually released.

5. The tester of claim 1 wherein means is provided for measuring and displaying any emitted light from said sample in a sensed pulse mode.

6. The tester of claim 1 wherein means is provided for measuring and displaying any emitted light from said sample in a signal integrated mode.

7. The tester of claim 1 wherein is provided a battery pack for providing the power to said motor and electrical circuit for field testing.

* * * * *